United States Patent
Donovan

(12)
(10) Patent No.: US 6,368,605 B1
(45) Date of Patent: *Apr. 9, 2002

(54) METHOD FOR TREATING CANCER WITH A NEUROTOXIN TO IMPROVE PATIENT FUNCTION

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/631,030

(22) Filed: Aug. 2, 2000

Related U.S. Application Data

(62) Division of application No. 09/454,842, filed on Dec. 7, 1999, now Pat. No. 6,139,845.

(51) Int. Cl.$^7$ ........................ A61K 39/08; A61K 39/00; A61K 39/38; A61K 39/02; A61K 38/00

(52) U.S. Cl. ............................... 424/239.1; 424/184.1; 424/234.1; 424/247.1; 424/236.1; 514/2; 530/350

(58) Field of Search ...................... 424/184.1, 236.1, 424/234.1, 247.1, 239.1; 514/2; 530/350

(56) References Cited

U.S. PATENT DOCUMENTS 5,766,605 A 6/1998 Sanders et al.

FOREIGN PATENT DOCUMENTS

| GB | 2142032 | 1/1985 |
|----|---------|--------|
| WO | 95 17904 | 7/1995 |

OTHER PUBLICATIONS

Bagshawe, K.D., et al.; Anitbody Directed Enzyme Prodrug Therapy (Adept): Clinical Report; *Disease Markers;* vol. 9:233–238 (1991).

Bagshawe, K.D., et al.; A Cytotoxic Agent can be Generated Selectively at Cancer Sites; *Br. J. Cancer;* 58:700–703 (1988).

Bryan, M.; Glomus Tumors; Dept. of Otolaryngology, UTMB; 10 pages (Jan. 11, 1995).

Eccles, S.A., et al.; Regression of Established Breat Carcinoma Xenografts with Antibody–Directed Enzyme Prodrug Therapy Against–c–erbB2 p185; *Cancer Research;* 54:5171–5177 (Oct. 1, 1994).

Heppner, F.; New Technologies to Combat Malignant Tumours of the Brain; *Anticancer Research;* 2:101–110 (1982).

Jankovic, J., et al., editors; *Therapy with Botulinum Toxin;* Marcel Dekker, Inc. publisher; p. 45 (1994).

Lemmon, J.J. et al., et al.; Anaerobic Bacteria as a Gene Delivery System to Tumors; *Proceedings of the American Association for Cancer Research;* vol. 35:374 (Mar. 1994).

Lin, J.C., et al.; Cardiac Pheochromocytoma: Resection After Diagnosis by 111–Indium Octreotide Scan; *Ann Thorac Surg* (1999); 67:555–558.

Naumann, M., et al.; Botulinum Toxin in the Treatment of Neurological Disorders of the Autonomic Nervous System; *Arch Neurol* (Aug. 1999); 56:914–916.

Ragona, R.M., et al.; Management of Parotid Sialocele with Botulinum Toxin; *Laryngoscope;* (Aug. 1999); 109: 1344–1346.

Sanchez–Prieto, J., et al.; Botulinum Toxin A Blocks. Glutamate Exocytosis from Guinea–Pig Cerebral Cortical Synaptosomes; *Eur. J. Biochem.* (1987); 165:675–681.

Schweitzer, E.S., et al.; Inhibition of Regulated Catecholamine Secretion from PC12 Cells by the $Ca^{2+}$/Calmodulin Kinase II Inhibitor KN–62; *Journal of Cell Science;* (1995); 108;2619–2628.

Sigma; *Biochemicals and Reagents for Life Science Research;* p. 187–188. 1998/1999.

Walther, M.M., et al.; Pheochromocytoma: Evaluation, Diagnosis, and Treatment; *World J Urol* (1999); 17:35–39.

Warwar, R.E., et al.; Coexistence of 3 Tumors of Neural Crest Origin; *Arch Ophthalmol* (Sep. 1998); 116:1241–1243.

Williamson, L.C., et al.; Clostridial Neurotoxins and Substrate Proteolysis in Intact Neurons; *The Journal of Biological Chemistry* (Mar. 29, 1996); vol. 271, No. 13; pp. 7694–7699.

Manger, W.M., et al.; *Clinical and Experimental Pheochromocytoma;* Second Edition; Blackwell Science, Inc. publisher (1996).

Robinson, R.; *Tumours that Secrete Catecholamines—Their Detection and Clinical Chemistry;* John Wiley and Sons, Ltd. publisher (1980).

Springer, C.J., et al; Ablation of Human Choriocarcinoma Xenografts in Nude Mice by Anitbody–Directed Enzyme Prodrug (ADEPT) with Three Novel Compounds; *Eur. J. Cancer;* 27(11): 1361–1366 (1991).

Xu, T., et al.; Kinetic Studies of Ca2+ Binding and Ca2+ Clearance in the Cytosol of Adrenal Chromaffin Cells; *Biophysical Journal;* vol. 73:532–535 (Jul. 1997).

B. Anabel et al: "Dual effects of botulinum neurotoxin A on the secretory stages of chromaffin cells." Euro J. Neuro 10:3369–3378; 1998.

F. Patrick et al: "Blockade by botulinum neurotoxin B of catechalamine release from adrenchromaffin cells correlates with its cleavage of synaptobrevin and a homologue present on the granules." Biochem, vol. 34, No. 16, 1995, pp. 5494–5503.

*Primary Examiner*—Anthony C. Caputa
*Assistant Examiner*—Alana M. Harris
(74) *Attorney, Agent, or Firm*—Martin A. Voet; Robert J. Baran; Carlos A. Fisher

(57) ABSTRACT

A method for reducing a catecholamine secretion from a cholinergically innervated, functional chromaffin body, such as a paraganglioma or hyperplasic adrenal medulla, by direct, local administration of a neurotoxin, such as a botulinum toxin.

9 Claims, No Drawings

METHOD FOR TREATING CANCER WITH A NEUROTOXIN TO IMPROVE PATIENT FUNCTION

This application is a divisional of Ser. No. 09/454,842, filed Dec. 7, 1999, now U.S. Pat. No. 6,139,845.

BACKGROUND

The present invention relates to methods for treating neoplasms. In particular the present invention relates to methods for treating catecholamine secreting neoplasms, both benign and cancerous, as well as hyperplasic chromaffin cells by local administration of a neurotoxin.

Adrenal Medulla

The adrenal or suprarenal glands are small, triangular-shaped structures located on top of the kidneys. Each adrenal gland comprises an adrenal cortex or outer portion and an adrenal medulla or inner portion. The cortex surrounds and encloses the medulla.

The adrenal cortex secrets the hormones cortisol and aldosterone. Cortisol is produced during times of stress, regulates sugar usage, and is essential for maintenance of normal blood pressure. Aldosterone is one of the main regulators of salt, potassium and water balance. If both adrenal glands are removed cortisol and aldosterone replacement therapy is mandatory.

The adrenal medulla secretes the catecholamines adrenalin (synonymously epinephrine) and noradrenalin (synonymously norepinephrine). These hormones are important for the normal regulation of a variety of bodily functions, including stress reaction, when they cause an increase in blood pressure, the pumping ability of the heart, and the level of blood sugar. Removal of the adrenal medulla results in little or no hormonal deficiency because other glands in the body can compensate. Contrarily, excessive catecholamine production can be life threatening.

In the normal adult male about 85% of total catecholamine made by the adrenal medulla is adrenaline, with remaining 15% being noradrenalin. There is about 1.6 mg of catecholamine present per gram of medulla tissue. Most of the noradrenalin found in blood and urine comes not from the adrenal medulla but from postganglionic sympathetic nerve endings. If the freshly sectioned adrenal gland is placed in fixatives that contain potassium dichromate, the medulla turns brown and this is referred to as the chromaffin reaction, so named to suggest the affinity of adrenal medulla tissue for chromium salts. Hence, cells of the adrenal medulla are often called chromaffin cells. Chromaffin cells also exists outside the adrenal medulla, but usually secrete only noradrenalin, not adrenaline The adrenal medulla can be viewed as a sympathetic ganglion innervated by preganglionic cholinergic nerve fibers. These nerve fibers release acetylcholine which causes secretion of catecholamines (primarily adrenaline) by a process of exocytosis from the chromaffin cells of the adrenal medulla. The normal adrenal medulla is innervated by the splanchnic nerve, a preganglionic, cholinergic branch of the sympathetic nervous system. The activity of the adrenal medulla is almost entirely under such cholinergic nervous control.

Chromaffin Cell Tumors

Chromaffin cells (including the chromaffin cells of the adrenal medulla) and sympathetic ganglion cells have much in common as they are both derived from a common embryonic ancestor, the sympathagonium of the neural crest, as shown diagrammatically below. Examples of the types of neoplasms which can arise from each these cell types is shown in brackets. Each of the cell types shown can potentially secrete catecholamines.

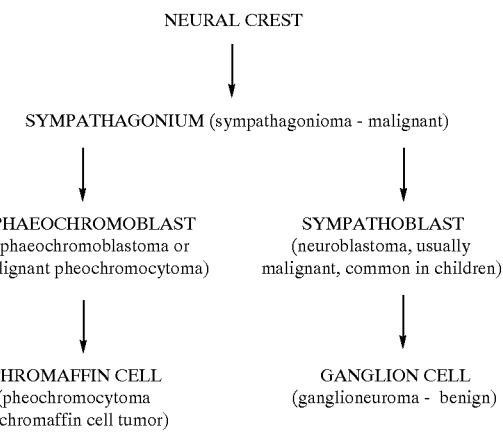

While most chromaffin cell neoplasms occur in the adrenal medulla, ectopic and multiple location chromaffin cell tumors are known, occurring most commonly in children.

1. Paragangliomas

A paraganglia (synonymously, chromaffin body) can be found in the heart, near the aorta, in the kidney, liver, gonads, and other places and is comprised of chromaffin cells which apparently originate from neural crest cells and which have migrated to a close association with autonomic nervous system ganglion cells. A paraganglioma is a neoplasm comprised of chromaffin cells derived from a paraganglia. A carotid body paraganglioma is referred to as a carotid paraganglioma, while an adrenal medulla paraganglioma is called a pheochromocytoma or a chromaffinoma.

The carotid body is often observed as a round, reddish-brown to tan structure found in the adventitia of the common carotid artery. It can be located on the posteromedial wall of the vessel at its bifurcation and is attached by ayer's ligament through which the feeding vessels run primarily from the external carotid. A normal carotid body measures 3–5 mm in diameter. Afferent innervation appears to be provided through the glossopharyngeal nerve (the ninth cranial nerve). The glossopharyngeal nerve supplies motor fibers to the stylopharyngeus, parasympathetic secretomotor fibers to the parotid gland and sensory fibers to inter alia the tympanic cavity, interior surface of the soft palate and tonsils). Histologically, the carotid body includes Type I (chief cells with copious cytoplasm and large round or oval nuclei. The cytoplasm contains dense core granules that apparently store and release catecholamines. The normal carotid body is responsible for detecting changes in the composition of arterial blood.

Carotid paragangliomas are rare tumors overall but are the most common form of head and neck paraganglioma. The treatment of choice for most carotid body paragangliomas is surgical excision. However, because of their location in close approximation to important vessels and nerves, there is a very real risk of morbidity(mainly cranial nerve X-XII deficits and vascular injuries) and mortality which is estimated as 3–9%. Tumor size is important because those greater than 5 cm in diameter have a markedly higher incidence of complications. Perioperative alpha and beta adrenergic blockers are given (if the carotid paraganglioma is secreting catecholamines) or less preferably angiographic embolization preoperatively. Radiotherapy, either alone or in conjunction with surgery, is a second consideration and an area of some controversy. Unfortunately, due to location and/or size, paragangliomas, including carotid paragangliomas can be inoperable.

2. Pheochromocytomas

Pheochromocytomas occur in the adrenal medulla and cause clinical symptoms related to excess catecholamine production, including sudden high blood pressure (hypertension), headache, tachycardia, excessive sweating while at rest, the development of symptoms after suddenly rising from a bent-over position, and anxiety attacks. Abdominal imaging and 24 hour urine collection for catecholamines are usually sufficient for diagnosis. Catecholamine blockade with phenoxybenzamine and metyrosine generally ameliorates symptoms and is necessary to prevent hypertensive crisis during surgery, the current therapy of choice. Standard treatment is laparoscopic adrenalectomy, although partial adrenalectomy is often used for familial forms of pheochromocytoma. Malignant (cancerous) pheochromocytomas are rare tumors.

Pheochromocytomas have been estimated to be present in approximately 0.3% of patients undergoing evaluation for secondary causes of hypertension. Pheochromocytomas can be fatal if not diagnosed or if managed inappropriately. Autopsy series suggest that many pheochromocytomas are not clinically suspected and that the undiagnosed tumor is clearly associated with morbid consequences.

The progression of changes in the adrenal medulla can be from normal adrenal medulla to adrenal medullary hyperplasia (a generalized increase in the number of cells and size of the adrenal medulla without the specific development of a tumor) to a tumor of the adrenal medulla (pheochromocytoma).

Treatment of a pheochromocytoma is surgical removal of one or both adrenal glands. Whether it is necessary to remove both adrenal glands will depend upon the extent of the disease. Patients who have had both adrenal glands removed must take daily cortisol and aldosterone replacement. Cortisol is replaced by either hydrocortisone, cortisone or prednisone and must be taken daily. Aldosterone is replaced by oral, daily fludrocortisone (Florineftm). Increased amounts of replacement hydrocortisone or prednisone are required by such patients during periods of stress, including fever, cold, influenza, surgical procedure or anesthesia.

3. Glomus Tumors

Glomus tumors (a type of paraganglioma) are generally benign neoplasms, also arising from neuroectodermal tissues, found in various parts of the body. Glomus tumors are the most common benign tumors that arise within the temporal bone and fewer than five per cent of them become malignant and metastasize. Glomus tumors arise from glomus bodies distributed along parasympathetic nerves in the skull base, thorax and neck. There are typically three glomus bodies in each ear. The glomus bodies are usually found accompanying Jacobsen's (CN IX) or Arnold's (CN X) nerve or in the adventitia of the jugular bulb. However, the physical location is usually the mucosa of the promontory (glomus tympanicums), or the jugular bulb (glomus jugulare).

The incidence of glomus jugulare tumors is about 1:1, 300,000 population and the most striking bit of epidemiology is the predominant incidence in females with the female:male incidence ratio being at least 4:1. Catecholamine secreting (i.e. functional) tumors occur in about 1% to 3% of cases.

Glomus tumors have the potential to secrete catecholamines, similar to the adrenal medulla which also arises from neural crest tissue and can also secrete catecholamines. The neoplastic counterpart of a glomus tumor in the adrenal gland is the pheochromocytoma, and glomus tumors have been referred to as extra-adrenal pheochromocytoma. Catecholamine secreting glomus tumors can cause arrhythmia, excessive perspiration, headache, nausea and pallor.

Glomus tumors can arise in different regions of the skull base. When confined to the middle ear space, they are termed glomus tympanicum. When arising in the region of the jugular foramen, regardless of their extent, they are termed glomus jugulare. When they arise high in the neck, extending towards the jugular foramen, they are termed glomus vagale. When they arise in the area of the carotid bifurcation, they are called carotid body tumors. Other known sites of glomus tumors include the larynx, orbit, nose, and the aortic arch.

Glomus Jugulare tumors are the most common tumors of the middle ear. These tumors tend to be very vascular and are fed by branches of the external carotid artery. The symptoms of a glomus jugulare tumor include hearing loss with pulsatile ringing in the ear, dizziness, and sometimes ear pain. The patient can have a hearing loss due possibly to blockage of the middle ear, but also there can be a loss of hearing due to nerve injury from the tumor mass. Cranial nerve palsies of the nerves which control swallowing, gagging, shoulder shrugging and tongue movement can all be part of the presentation of glomus jugulare tumors. When the tympanic membrane is examined a red/blue pulsatile mass can often be seen. Symptoms are insidious in onset. Because of the location and the vascular nature of the tumors, a most common complaint is pulsatile tinnitus. It is believed that the tinnitus is secondary to mechanical impingement on the umbo is most cases. Other common symptoms are aural fullness, and (conductive) hearing loss.

Current therapy for a catecholamine secreting glomus tumor is irradiation and/or surgical ablation, preceded by administration of alpha and beta blockers. Treatment for glomus jugulare tumors includes administration of alpha and beta blockers. X-ray therapy can be used to improve symptoms even if the mass persists. It is also possible to embolize the tumor with materials which block its blood supply, however this procedure has associated problems with causing swelling of the tumor which can compress the brain stem and cerebellum as well as releasing the catecholamines from the cells which die when they lose their blood supply. Surgery can be carried out upon small tumors appropriately located. The complications of surgery for a glomus jugulare tumor are persistent leakage of cerebrospinal fluid from the ear and also palsy of one of the cranial nerves controlling face movement, sensation or hearing.

Even though the surgery may be successful glomus jugulare tumors are somewhat problematic because they have a high recurrence rate and may require multiple operations. Surgical ablation carries the risk of morbidity due mainly to iatrogenic cranial nerve deficits and CSF leaks. Lack of cranial nerve preservation is probably the most significant objection to surgical intervention because of the associated morbidity of lower cranial nerve deficits. Radiotherapy also has serious complications, including osteoradionecrosis of the temporal bone, brain necrosis, pituitary-hypothalamic insufficiency, and secondary malignancy. Other postoperative complications include CSF leaks, aspiration syndromes, meningitis, pneumonia and wound infections Botulinum Toxin The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type $A^1$ is a $LD_{50}$ in mice. One unit (U) of botulinum toxin is defined as the $LD_{50}$ upon intraperitoneal injection into female Swiss Webster mice weighing 18–20 grams each. Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species s that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmifters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

It has been reported that botulinum toxin type A has been used in clinical settings as follows:
  (1) about 75–125 units of BOTOX® per intramuscular injection (multiple muscles) to treat cervical dystonia;
  (2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than as BOTOX®, possibly because of the higher protein load injected to achieve an effective dose of botulinum toxin type B.

Acetvlcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secrete the neurotransmitter norepinephine. In most instances acetylcholine has an excitatory effect. However, acetylcholine is known to have inhibitory effects at some of the peripheral parasympathetic nerve endings, such as inhibition of the heart by the vagus nerves.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore is an effective, non-surgical ablation, non-radiotherapy therapeutic method for treating hyperplasic and/or neoplasmic, catecholamine secreting chromaffin cells, including paragangliomas, such as glomus tumors.

SUMMARY

The present invention meets this need and provides an effective, non-surgical ablation, non-radiotherapy therapeutic method for treating hyperplasic and/or neoplasmic, catecholamine secreting chromaffin cells, including paragangliomas, such as glomus tumors.

The present invention includes within its scope a method for treating a functional neoplasm or functional chromaffin body by local administration of a neurotoxin to a neoplasm thereby reducing a catecholamine secretion from the neoplasm. As used herein "functional" means secreting a catecholamine, "local administration" means direct injection of the neurotoxin into or to the local area of the neoplasm and "neoplasm" (or synonymously "tumor") means an abnormal tissue that grows more rapidly than normal and which may be either a benign tumor or a malignant tumor, that is a cancer). Systemic routes of administration, such as oral and intravenous routes of administration, are excluded from the scope of the present invention. The functional neoplasm treated can be a paraganglioma or a glomus tumor.

The neurotoxin can be locally administered in an amount of between about $10^{-3}$ U/kg and about 35 U/kg. More preferably, the neurotoxin can be locally administered in an amount of between about $10^{-2}$ U/kg and about 25 U/kg. Most preferably, the neurotoxin is administered in an amount of between about $10^{-2}$ U/kg and about 15 U/kg and in a particularly preferred embodiment of the present invention the neurotoxin is administered in an amount of between about 1 U/kg and about 10 U/kg. The neurotoxin can be a neurotoxin made by a Clostridial bacterium, such as a Clostridium botulinum, Clostridium butyricum or Clostridium beratti bacterium.

Additionally, the neurotoxin can be a modified neurotoxin, that is the neurotoxin can have at least one of its amino acids deleted, modified or replaced, as compared to a native neurotoxin. Thus, the neurotoxin can be a recombinant produced neurotoxin or a derivative or fragment thereof.

Preferably, the neurotoxin used in the present method is a botulinum toxin, such as one of the botulinum toxin serotypes A, B, $C_1$, D, E, F or G. Most preferably, the neurotoxin is botulinum toxin type A.

A preferred method according to the present invention for treating a secretory neoplasm can have the step of local administration of a therapeutic amount of a botulinum toxin to a secretory neoplasm of a human patient, thereby reducing a secretion from the neoplasm. The secretion is a catecholamine secretion and the secretory tumor can be a functional paraganglioma. Furthermore, the functional paraganglioma can be, for example, a glomus tympanicum, a glomus jugulare, glomus vagale and a carotid body tumor.

The present invention also includes a method for improving patient function, the method comprising the step of administering a neurotoxin to a functional paraganglioma of a human patient, thereby improving patient function as determined by improvement in one or more of the factors of reduced pain, reduced time spent in bed, increased ambulation, healthier attitude and a more varied lifestyle.

A further method within the scope of the present invention for treating a secretion of a patient can have the step of administering to the patient an effective amount of a botulinum toxin in order to reduce the secretion, wherein the secretion is a catecholamine secretion. And the secretion can be an endocrine secretion from a chromaffin cell. Notably, the chromaffin cell can be a hyperplasic and/or hypertonic chromaffin cell and the secretion can be a cholinergic influenced secretion.

An additional method within the scope of the present invention can be a method for treating a cholinergic influenced, endocrine, catecholamine chromaffin cell secretion of a human patient by administering to a human patient a therapeutically effective amount of botulinum toxin type A in order to reduce the secretion.

The present invention also includes a method for treating a gland by administering to a gland a botulinum toxin thereby reducing a secretory activity of the gland, wherein the gland is a catecholamine secreting gland. The gland can be an excessively secreting gland and/or the gland can be influenced by the cholinergic nervous system. Additionally, the botulinum toxin can be administered by injection into the gland or into the local area of the gland.

Another preferred method within the scope of the present invention is a method for treating an excessively catecholamine secreting gland, the method comprising the step of injecting an excessively catecholamine secreting, cholinergic nervous system influenced gland or local gland area of a human patient with a therapeutically effective amount of botulinum toxin type A in order to reduce the excessive catecholamine secretion. The invention also includes a method for treating an endocrine disorder, the method comprising the step of administering a neurotoxin to a mammal, thereby reducing an excessive secretion of an endocrine gland. Finally, the invention encompasses a method for treating an adrenal disorder, the method comprising the step of administering a neurotoxin to an adrenal gland of a mammal, thereby reducing an excessive secretion of an adrenal gland.

DESCRIPTION

The present invention is based upon the discovery that various excessively secreting chromaffin cells and chromaffin bodies can be treated in vivo with a botulinum toxin to reduce the secretory activity. The target tissue is cholinergically innervated or susceptible to high toxin dosing such that the proteolytic light chain of the toxin is internalized by a cholinergic neuron which influences the activity of a chromaffin cell and/or by the target secretory chromaffin cell.

Thus, cholinergically innervated functional paragangliomas, pheochromocytomas and glomus tumors can be treated by local administration of a neurotoxin, such as a botulinum toxin. By local administration it is meant that the neurotoxin is administered directly to, into, or to the vicinity of, the tumor or local tumor area to be treated. Local administration includes intratumor injection of a neurotoxin. Non-cancerous (benign), cancerous (malignant) hyperplasic and/or hypertonic catecholamine secreting tissues can be treated by a method within the scope of the present invention. Nodular or diffuse hyperplasia which precedes pheochromocytoma can also be treated by the present method. Hence, upon early diagnosis, botulinum injection can be used to reduce catecholamine secretion by hyperplasic, cholinergically innervated chromaffin cells.

I have discovered that a particular neurotoxin, botulinum toxin, can be used with dramatic ameliorative effect to treat a catecholamine secretory activity of paragangliomas, thereby significantly superseding current surgical and radiotherapy therapeutic oncological methods with regard to such neoplasms. Significantly, a single administration of the botulinum toxin can substantially reduces the tachycardia, headache, hypertension, and other catecholamine excess symptoms which can accompany a functional paraganglioma.

The route of administration and amount of botulinum toxin administered can vary widely according to the particular oncologic disorder being treated and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14$^{th}$ edition, published by McGraw Hill). For example, to treat a tinnitus due to a middle ear glomus tumor, a solution of botulinum toxin type A complex can be endoscopically administered intramuscular directly to the tumor, thereby substantially avoiding entry of the toxin into the systemic circulation.

The specific dosage appropriate for administration is readily determined by one of ordinary skill in the art according to the factor discussed above. The dosage can also depend upon the size of the tumor to be treated or denervated, and the commercial preparation of the toxin. Additionally, the estimates for appropriate dosages in humans can be extrapolated from determinations of the amounts of botulinum required for effective denervation of other non-neoplastic tissues. Thus, the amount of botulinum A to be injected is proportional to the mass and level of activity of the neoplasm to be treated. Generally, between about 0.01 and 35 units per kg of patient weight of a botulinum toxin, such as botulinum toxin type A, can be administered to effectively accomplish a toxin induced neoplastic atrophy upon administration of the neurotoxin at or to the vicinity of the neoplasm. Less than about 0.01 U/kg of a botulinum toxin does not have a significant therapeutic effect upon a functional (i.e. catecholamine secreting) neoplasm, while more than about 35 U/kg of a botulinum toxin approaches a toxic dose the neurotoxin. Careful placement of the injection needle and a low volume of neurotoxin used prevents significant amounts of botulinum toxin from appearing systemically. A more preferred dose range to a functional paraganglioma is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the neoplasm to be treated and the administration route chosen. Botulinum toxin type A is a preferred botulinum toxin serotype for use in the methods of the present invention.

The main site of action of botulinum toxin is the neuromuscular junction where the toxin binds rapidly and prevents the release of acetylcholine. Thus, while it is known that the botulinum toxins have a known binding affinity for cholinergic, pre-synaptic, peripheral motor neurons, I have discovered that the botulinum toxins can also bind to and translocate into a wide variety of non-neuronal secretory cells, where the toxin then acts, in the known manner, as an endoprotease upon its respective secretory vessel-membrane docking protein. Because of the lower affinity of the botulinum toxins for secretory cells, such as chromaffin cells, the toxin is preferably injected into secretory or glandular tissues to provide a high local concentration of the toxin. Thus, the present invention is applicable to the treatment of secretory, including catecholamine secreting, chromaffin cells and tumors located throughout the body, including secretory tumors with little or no cholinergic innervation.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection.

A route for administration of a neurotoxin according to the present disclosed invention for treating a cancer can be selected based upon criteria such as the solubility characteristics of the neurotoxin toxin chosen as well as the amount of the neurotoxin to be administered. The amount of the neurotoxin administered can vary widely according to the particular disorder being treated, its severity and other various patient variables including size, weight, age, and responsiveness to therapy. For example, the extent of the neoplasm influenced is believed to be proportional to the volume of neurotoxin injected, while the quantity of the denervation is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14th edition, published by McGraw Hill).

The present invention includes within its scope the use of any neurotoxin which has a long duration therapeutic effect when locally applied to a functioning paraganglioma of a patient. For example, neurotoxins made by any of the species of the toxin producing Clostridium bacteria, such as Clostridium botulinum, Clostridium butyricum, and Clostridium beratti can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide neoplasmic atrophy and remission for 27 months or longer in humans.

It is known that catecholamine release from permeabalized adrenal medulla cells can be inhibited by a botulinum toxin. Additionally, it is known that release of insulin from permeabalized (as by electroporation) insulin secreting cells can be inhibited by a botulinum toxin. When in vitro, the cell membranes of these non-nerve cells can be permeabalized to assist introduction of a botulinum toxin into the cell's cytosol due to the lack of cell surface receptors for a botulinum toxin. Thus, botulinum toxin type B apparently inhibits insulin secretion by cleaving synaptobrevin present in the insulin secreting cell line HIT-15. Boyd R. S., et al *The Effect of Botulinum Neurotoxin-B On Insulin Release From a Beta Cell*, Mov Disord 10(3):376 (1995). It is the inventor's contention that a botulinum toxin can block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention, non-cholinergic nerve fibers as well as non or poorly innervated secretory neoplasms can be treated by use of an appropriately higher concentration of a botulinum toxin to bring about therapeutic atrophy of secretory neoplasms (i.e. treatment of functional (catecholamine secreting) paragangliomas) and hyperplasic chromaffin cells.

In the normal adrenal medulla, the catecholamine secretion rate is controlled by the activity of the nerves stimulating the chromaffin cells. Contrary to the general belief that the pheochromocytomas are not innervated and that the release of catecholamines from such tumors is not under nervous control, there is evidence for cholinergic innervation of such tumors. For example, electron microscopy has demonstrated a nerve with small synaptic vesicles in contact with cells containing catecholamine vesicles. Additionally, the sudden secretion of catecholamines from a pheochromocytomas into the circulation precipitated by an emotional upset, hypotension or hyperventilation points to a nervous system influence on the secretion. Furthermore, the tilting a patient with a pheochromocytoma from a horizontal to an upright position has been shown to cause an exaggerated increase in urinary norepinephrine not seen in subjects with such a tumor and this may effect result from (a) a mechanical effect (i.e. compression of the catecholamine rich tumor) (b) reflex activation of the sympathetic system in which adrenergic system increased amounts of catecholamines may have accumulated in the nerve endings of a patient with a pheochromocytoma and/or (b) activation of existing pheochromocytoma innervation.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to a chromaffin body of a human patient. In its most preferred embodiment, the present invention is practiced by direct injection into the neoplasm or to the local area of the neoplasm of botulinum toxin type A. It has been reported that at the neuroglandular junction, the chemical denervation effect of a botulinum toxin, such as botulinum toxin type A, has a considerably longer duration of action, i.e. 27 months vs. 3 months.

The present invention does include within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for chromaffin and neoplasm cells types.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

EXAMPLES

The following examples provide those of ordinary skill in the art with specific preferred methods within the scope of the present invention for carrying out the present invention and are not intended to limit the scope of what the inventor regards as his invention One or two port endoscopy of the middle ear can be carried out. Thus, anatomical structures can be visualized by transmeatal or transtympanic rigid scopes of different angles and by a flexible scope in the eustachian tube. Three endoscopic routes to the middle ear can be used, these being: (1) transmeatal after raising a tympanomeatal flap, (2) transtympanic through a tympanic incision, and (3) the non-invasive through the preformed channel of the eustachian tube.

Example 1

Endoscopic Examination of A Middle Ear Glomus Tumor

A transtympanic endoscope can be used to view of the tympanic cavity. A flexible, steerable scope with an outside diameter of 0.8 mm (12,000 pixels; angle of view, 70°; total length, 650 mm; deflection angle, 90°; and length of deflectable part 25 mm) obtained from Micromed Co, Dornbirn, Austria can be used for transtubal endoscopy. The patient's head can be positioned in 30° lateral decubitus. The transtubal scope can be introduced through a tubal catheter placed at the pharyngeal orifice of the eustachian tube under endoscopic guidance (rigid 70° scope) through the contralateral nasal airway. After removing the rigid scope, the flexible steerable scope can be advanced into the middle ear through the tubal catheter. Successful advancement of the scope to the middle ear requires an adequate width of the tubal isthmus (mean, 1.0 mm wide and 2 mm high).

Transmeatal or transtympanic endoscopy can be performed using a rigid scope. Depending on the approach chosen, the outside diameter of the scope can be either 2.3 or 1.9 mm, with angles of 0°, 30°, or 70° (Karl Storz, Tuttlingen, and Aesculap). For the transmeatal approach, the tympanic cavity can be opened by endoscopically raising a tympanomeatal flap so that the scope can enter the posterior part of the cavity below the incudostapedial joint. For the transtympanic approach, radial incisions can be made in the tympanic membrane either between the posterosuperior and the posteroinferior quadrant or in the anteroinferior quadrant, depending on the region of interest. Images can be recorded on a digital image recording device from S-VHS video sources (Digi-Still Unit and S-VHS Video Recorder; Sony, Vienna, Austria).

The field of view available depends on the angle of the scope (0°, 30°, or 70°). The 0° scopes can provide visualization only of the long process of the incus and the medial wall (labyrinthine wall). The 30° scopes can afford a larger view in all directions. The field of view can extend to the facial canal with the scope directed upward, to the round window niche with the scope directed downward, to the tympanic sinus with the scope directed posteriorly, and to the cochleariform process with the scope directed anteriorly. The 70° scope can offer an even wider view of the tympanic cavity. With these, the tympanic chord and the aditus ad antrum can be seen above, the hypotympanum below, the lateral sinus and facial recess posteriorly, and the tympanic orifice of the tube anteriorly.

With a transtubal endoscope, the isthmus can be successfully negotiated and passage aided by subtly maneuvering and turning the scope tip. Once the steerable scope has reached the protympanum, it can be advanced along 2 alternative routes: (1) above the tensor tendon into the epitympanum and then along the tegmen to the mastoid antrum; or (2) below the tensor tendon into the mesotympanum toward the incudostapedial joint and then either (a) medial to the incus and above the stapes into the aditus ad antrum or (b) lateral to the incus toward the tympanic chord or (c) below the stapes toward the lateral sinus. As the scope is advanced through the mesotympanum, it passes the entire tympanic membrane, which forms the lateral wall and can be inspected in its entire extension. Along the routes described, the flexible scope can be easily maneuvered past the ossicles without injuring them.

In each of the following examples, the specific amount of BOTOX® administered depends upon a variety of factors to be weighed and considered within the discretion of the attending physician and in each of the examples insignificant amounts of botulinum toxin appear systemically with no significant side effects.

Example 2

Treatment of Catecholamine Secreting Glomus Tumor

A female patient, aged 58 presents with tachycardia, headache and elevated urine catecholamines metabolites. Adrenal function is normal. A benign, functional, middle ear glomus tumor is identified and is treated by endoscopic injection of from 10 unit to 100 units of BOTOX® into the tumor mass. Within 1–7 days serum catecholamines return to normal and remain so for the ensuing 2 to 24 months.

Other glomus tumors which have arisen from glomus bodies distributed along parasympathetic nerves in the skull base, thorax and neck can be likewise treated.

Example 3

Treatment of Catecholamine Secreting Carotid Paraganglioma

A 44 year old male patient with a neck mass is examined and a diagnosis of carotid paraganglioma is made. Grossly the carotid paraganglioma is dark, tan to purple in color and is fairly well circumscribed with a very thin fibrous capsule, presented as a non-tender neck mass located just anterior to the sternocleidomastoid muscle at the level of the hyoid. The patient shows symptoms associated with catecholamine production, such as fluctuating hypertension, blushing and palpitations. Screening for urinary metanephrines and serum catecholamines is positive. Perioperative alpha and beta adrenergic blockers are given. The approach is transcervical and from 10 unit to 150 units of BOTOX® is injected into the mass of the tumor which is in proximity to or innervated by the glossopharyngeal nerve. Within 1–7 days serum catecholamines return to normal and remain so for the ensuing 2 to 27 months.

Example 4

Treatment of Hyperplasic Adrenal Medulla

A 62 year old female is admitted with symptoms of excessive catecholamine production, including tachycardia and hypertension. The patient abstains from bananas, vanilla, coffee, tea, cocoa, chocolate, cola beverages, or medications such as tranquilizers and nose sprays for colds for 2 days. Measurement of adrenalin and noradrenalin breakdown products in blood and a 24-hour collection of urine confirms the existence of an excessive catecholamine secretion. A computerized tomographic scan (CT or MRI to provide a 3-dimensional picture of the adrenal gland), or a nuclear medicine scan is carried out to attempt determination of the location and size of the tumor. Biopsy reveals a precancerous, hyperplasic adrenal medulla. From 10 to 150 units of BOTOX® is injected endoscopically directly into the adrenal medulla. Within 1–7 days serum catecholamines return to normal and remain so for the ensuing 2 to 24 months.

Methods according to the invention disclosed herein has many advantages, including the following:

(1) the invention renders unnecessary many surgical procedures for effective treatment of functioning chromaffin bodies, including hyperplasic, hypertonic and neoplasmic catecholamine secreting tissues.

(2) systemic drug effects can be avoided by direct local application of a neurotoxin according to the present invention (3) the ameliorative effects of the present invention can persists for two years or longer from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local otic administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, in the preparation of a medicament for the treatment of a functioning chromaffin body disorder by local administration of the neurotoxin.

Accordingly, the spirit and scope of the following claims should not be limited to the descriptions of the preferred embodiments set forth above.

I claim:

1. A method for improving patient function, the method comprising the step of administering a botulinum toxin to a paraganglioma of a human patient, thereby improving patient function.

2. The method of claim 1, wherein the botulinum toxin is administered in an amount of between about $10^{-3}$ U/kg and about 35 U/kg.

3. The method of claim 1, wherein the botulinum toxin is administered in an amount of between about $10^{-2}$ U/kg and about 25 U/kg.

4. The method of claim 1, wherein the botulinum toxin is administered in an amount of between about $10^{-2}$ U/kg and about 15 U/kg.

5. The method of claim 1, wherein the botulinum toxin is administered in an amount of between about 1 U/kg and about 10 U/kg.

6. The method of claim 1, wherein the botulinum toxin is selected from the group consisting of botulinum toxin types A, B, $C^1$, D, E, F and G.

7. The method of claim 1, wherein the botulinum toxin is botulinum toxin type A.

8. The method of claim 1, wherein the botulinum toxin is locally administered by direct injection of the neurotoxin into the paraganglioma.

9. A method for improving patient function, the method comprising the step of administering a botulinum toxin type A to a paraganglioma of a human patient, thereby improving patient function.

* * * * *